United States Patent [19]

Hildebrandt et al.

[11] 3,976,060
[45] Aug. 24, 1976

[54] EXTENSION APPARATUS, ESPECIALLY FOR OSTEOTOMIC SURGERY

[75] Inventors: Jürgen J. Hildebrandt, Brunnthal; Paul Zahn, Riemerling; Alfred Nikolaus Witt, Gmund; Michael Jäger, Munich, all of Germany

[73] Assignee: Messerschmitt-Bolkow-Blohm GmbH, Munich, Germany

[22] Filed: Apr. 1, 1975

[21] Appl. No.: 564,067

[30] Foreign Application Priority Data
Apr. 9, 1974  Germany............................ 2417233

[52] U.S. Cl. ............................. 128/84 R; 128/92 R
[51] Int. Cl.² ............................................ A61F 5/04
[58] Field of Search ............. 128/84 R, 84 A, 84 B, 128/84 C, 83, 92 R, 92 G, 92 B, 92 BC, 92 EC, 87

[56] References Cited
UNITED STATES PATENTS

| | | | |
|---|---|---|---|
| 2,155,866 | 4/1939 | Longfellow......................... | 128/84 B |
| 2,391,693 | 12/1945 | Ettinger............................. | 128/84 B |
| 2,393,982 | 2/1946 | Giesen................................ | 128/84 B |
| 2,443,106 | 6/1948 | Grosso ............................... | 128/84 B |

*Primary Examiner*—John D. Yasko
*Attorney, Agent, or Firm*—W. G. Fasse; W. W. Roberts

[57] ABSTRACT

The present apparatus is especially constructed for osteotomic purposes. Bone extension means are movably supported in an elongated, slender housing. The extension means include an extension member movably extending out of said housing. Drive means are supported in the housing and operatively connected to the extension means. The drive means are energized through a source of power which may be either located in the housing itself, or it may be an external power source, such as a magnetic field. The power source is operatively connected to said drive means. Control means are supported in said housing to operate the drive means through said power source for moving the extension member. Sealing means seal the housing so as to provide an implantable structural unit.

16 Claims, 9 Drawing Figures

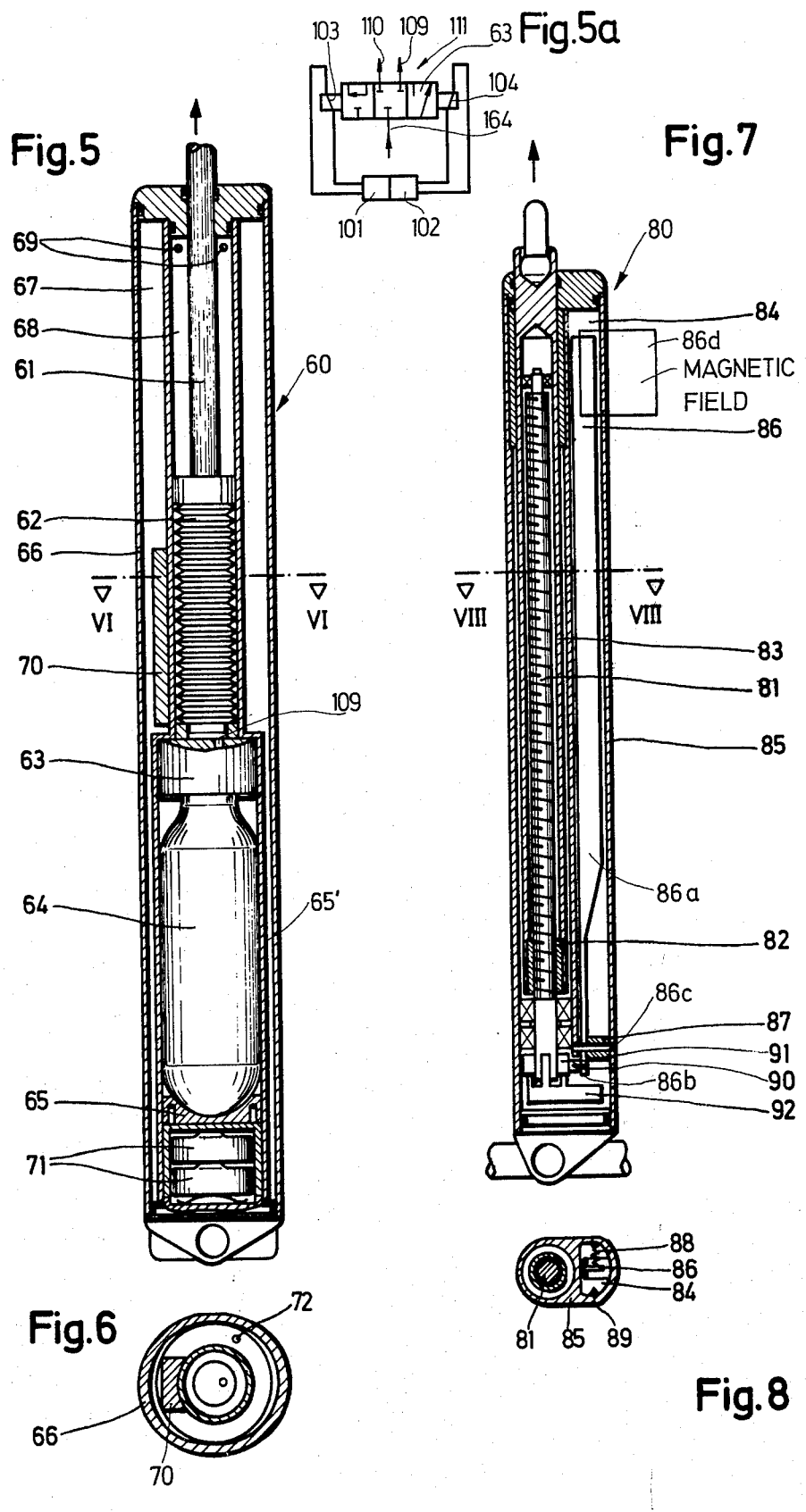

EXTENSION APPARATUS, ESPECIALLY FOR OSTEOTOMIC SURGERY

BACKGROUND OF THE INVENTION

The invention relates to an extension apparatus, especially for osteotomic surgery for the purpose of extending bones. This type of apparatus is also known as a "distraction device." However, in the following text, the apparatus will be referred to as an extending or extension means, which is employed for compensating differing lengths in the bone structure. Such differences in length may be in the nature of a birth defect or the result of an injury. Osteotomic surgery intends to correct such defects especially where the difference in length of limbs is substantial.

Devices of this type have the purpose to extend the two portions of a severed bone, which is fixed against lateral displacement in a continuous and/or in a stepwise manner. The extension must be such that during the entire treatment period the spacing between the severed bone portions is adjustable on the one hand with due regard to the desired lengthening and on the other hand, injury to the patient must be avoided.

Prior art devices for achieving the above purposes have been clinically tested. However, known devices and methods of the Anderson type require a prolonged bed confinement of the patient and thus involve all the disadvantages resulting from such confinement, for example, employing a so called Steinmann nail and a supracondyle extension bail for osteotomic extension purposes. A more recent method which has already been clinically tested is known as the Wagner extension osteotomy. According to this method the hollow bone is severed across its length. Two so called Schanz screws are inserted into the proximal and distal metaphyse in a percutaneous manner. The two bone portions are then slowly pulled apart with the aid of an extension apparatus. In the known Wagner method the patient himself may control the extension of the bone portions by means of a knurled handle forming part of the extension apparatus. The Wagner method does not require a prolonged immobilization of the patient who may leave the bed earlier than is required in case the supracondyle extension is employed. However, the Wagner method has the disadvantage that the Schanz screws require a percutaneous penetration or an open connection to the bone as well as the external attachment of the extension apparatus, whereby the danger of infection is increased. In addition, the chance of a mechanical fault or damage due to external influences such as impact, vibration, or the like is also increased. Besides, the Wagner apparatus is not quite suitable for the purpose of having the patient perform exercises. In other words, the patient may apply only a minimum load to the leg to which the apparatus is connected when the patient leaves the bed. However, it is well known that the healing process would be improved if the patient were able to move about in a less restrictive manner. Thus, even where the Wagner method is applied a prolonged hospitalization must be taken into account.

OBJECTS OF THE INVENTION

In view of the above it is the aim of the invention to achieve the following objects singly or in combination:

to overcome the drawbacks of the prior art, more specifically to provide an apparatus for osteotomy extension purposes which will permit a substantial reduction of the duration of hospitalization;

to provide a bone extension apparatus which will permit a more rigorous loading of the treated limb and thus allow more vigorous exercise than heretofore by reducing the lever effects present in prior art devices;

to reduce the bed confinement time and thus the hospitalization time of patients undergoing osteotomic surgery;

to provide an apparatus which will permit the precise adjustment of a bone extension or even an extension reduction whereby an automatic timing of the control may also be provided; and to construct the entire apparatus in such a manner that it will be implantable into the patient's body as an integral, structural unit.

SUMMARY OF THE INVENTION

The above objects have been achieved according to the invention by constructing an osteotomic extension apparatus according to the invention in such a manner that the extension means and a power drive means are both included in a sealed housing which forms an implantable structural unit. Preferably, and in order to reduce the danger of infection, an implantable power source is included in the housing as part of the power drive means. According to a still further embodiment of the invention, a control means which may be actuated externally is also part of the implanted apparatus. The implanted power drive may comprise an electrical motor having a rotor or it may be an electrical linear motor which is either driven by a power source, such as a battery or dry cell included in the implantable housing, or it may be driven by an external power source, such as a magnetic field located outside the body portion to be treated. The implantable electric motor drives preferably comprise a power source having a small weight to power ratio and a small size. Further, a reduction gear may also be part of the implantable unit, whereby the source of power is preferably a battery or a dry cell. The term "battery" is intended to include so called accumulators.

BRIEF FIGURE DESCRIPTION

In order that the invention may be clearly understood, it will now be described, by way of example, with reference to the accompanying drawings, wherein:

FIGS. 5 and 5a illustrate a further embodiment in which the extension member is driven by means of gas from a pressurized gas container and a bellows interconnected by a double three way valve;

FIG. 6 is a sectional view along section line VI—VI in FIG. 5;

FIG. 7 illustrates a sectional view through a further embodiment of an apparatus according to the invention in which a threaded spindle is rotated by means of an external energy source; and FIG. 8 is a sectional view along section line VIII—VIII in FIG. 7.

DETAILED DESCRIPTION OF EXAMPLE EMBODIMENTS

Figure 1:
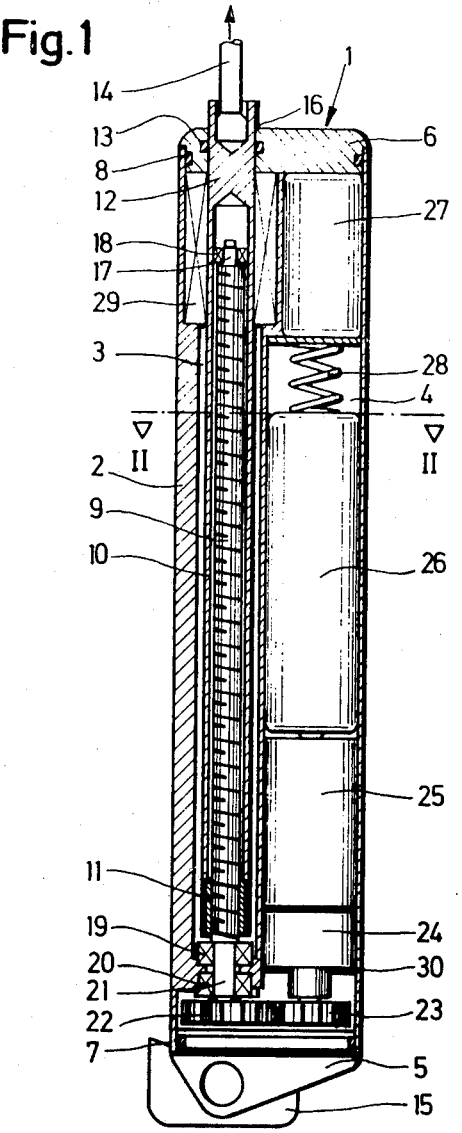
FIG. 1 is a longitudinal, sectional view of an apparatus according to the invention with an electric motor drive and a threaded spindle for moving an extension member.
Figure 2:
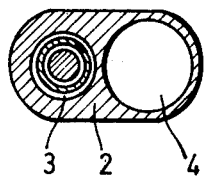
FIG. 2 is a sectional view through section line II—II in FIG. 1.

FIG. 1 illustrates a longitudinal sectional view through an extension apparatus 1 comprising an implantable housing 2 having a substantially oval cross section, as best seen in FIG. 2. The housing 2 is rigidly constructed, for example, of stainless steel and is stiff against bending. Two bores 3 and 4 extend longitudinally through the housing with the axes of these bores extending in parallel to each other. The housing 2 is sealed by a bottom 5 and by a cover 6. A proper sealing of the housing 2 may, for instance, be accomplished by employing sealing rings, such as O-rings 7 and 8 and providing a pressure fit between the housing and the cover, as well as between the housing and the bottom. The bottom 5 and the cover 6 may also be threaded to the housing to assure an air-tight and moisture-proof seal. Preferably, the housing will be enveloped by a coating, as shown at 33 in FIG. 3. The coating may, for instance, be made of an elastomeric material, such as polyurethane, silicone rubber, polyethylene and the like.

The extension or so called "distraction" is accomplished by means of a threaded spindle 9 supported for rotation at both ends and cooperating with a rotating sleeve 10, the lower end of which is provided with a threaded bushing surrounding the threaded spindle 9. The upper end of the sleeve 10 reaches out of the housing 2 and acts as an extension member or push rod 12. The cover 6 has a bore 16 guiding the extension member 12 in a sliding manner. A sealing 13 in the surface of the guiding bore 16 seals the housing. A connecting element 14 illustrated in a simplified manner is secured to the extension member 12. Similarly, a connecting element 15 is secured to the bottom 5. These connecting elements are used to secure the housing to a bone and thus to interconnect such bone ends with each other through the housing in a manner known as such.

The threaded spindle 9 is supported at its upper end by means of a bearing pin 17 held in a radial bearing 18. The sleeve 10 is axially displaceable relative to the radial bearing 18. The lower end of the extension member 12 is supported in an axial bearing 19 and in a further radial bearing 20 secured to a bearing pin 21. These bearings secure the spindle 9 against axial displacement in the housing 2.

An electric motor 25 drives the spindle 9 through a reduction gear 24 driving a gear wheel 23 which meshes with a further gear wheel 22, secured to the bearing pin 21 of the spindle 9. A battery 26, such as a dry cell or an accumulator provides the power for driving the motor 25, which may be switched on and off by means of an electronic control circuit 27, which is also suitable for reversing the direction of rotation of the motor 25. For this purpose, the electronic control circuit 27 comprises well known elements, for example, a magnetic switch which may be actuated by a magnetic field located externally of the housing 2 and also externally of the patient's body. The control circuit may be actuated in any other wireless way well known in the art. The internal power supply of the control circuit 27 may be provided by its own battery, not shown or it may be derived from the battery 26. The battery 26 could be soldered into the circuit or, as shown in the drawing, a spring 28 may be sufficient for maintaining a good contact between the battery 26 and the circuit or circuits which derive their power from the battery 26.

In order to reduce the load on the sliding guide 16 there is provided an anti-friction bearing or ball guide 29 securing the sleeve 10 relative to the housing 2. Such ball guide 29 takes up the forces which are radially effective on the sleeve 10 so that the load will be transmitted to the housing through the ball guide 29 rather than through the sleeve bearing type of guide 16.

The apparatus according to the invention in all of its illustrated embodiments has the advantage that after its removal from a patient's body upon completion of the bone extension, the apparatus may easily be prepared for use with another patient. The cover 6 and/or the bottom 5 is easily removed, whereupon all the elements in the bore 4 may be removed from the housing. If the bottom 5 is removed, it is necessary to also remove the retaining ring 30, which holds the elements in the bore 4 in position. With the parts removed, the spindle 9 may easily be returned to a starting position. Thus, parts requiring maintenance are easily accessible and parts requiring replacement, such as the battery 26 may easily be replaced. Incidentally, the sectional view of FIG. 2 illustrates the slender structure of the present extension apparatus.

Figure 3:
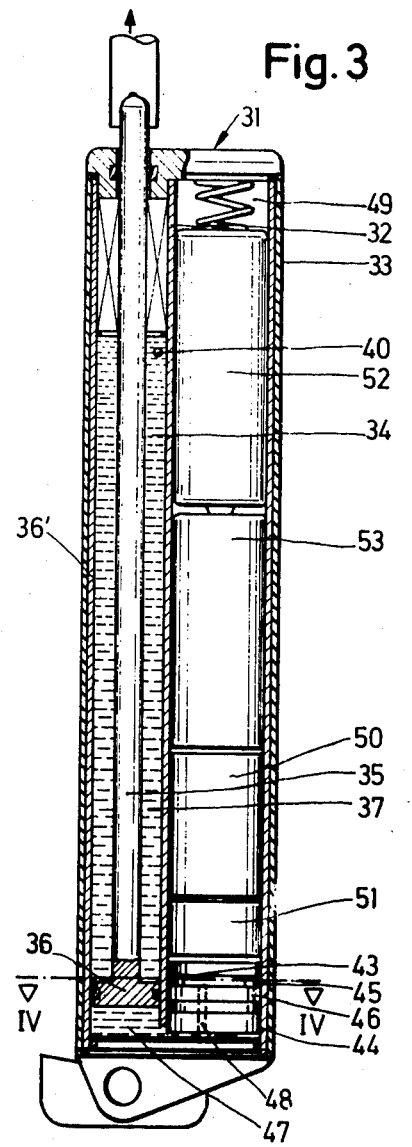
FIG. 3 is a view similar to that of FIG. 1, but illustrating a modification according to the invention in which the extension member is driven by a hydraulic pump which in turn is operated by an electric motor.
Figure 4:
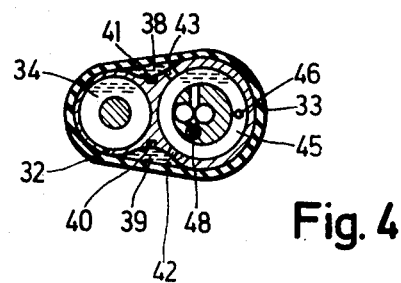
FIG. 4 is a sectional view along section line IV—IV in FIG. 3.

The embodiment of FIGS. 3 and 4 employs extension means comprising a piston cylinder arrangement instead of the spindle 9. The extension sleeve 10 of FIG. 1 is replaced by a piston rod 35 in FIG. 3. The piston rod is secured to a piston 36, which is slidable up and down in the cylinder 36' which forms part of the housing 32 of the extension apparatus 31. As mentioned, the housing is surrounded by an elastomeric soft material forming an envelope 33, for example, of a polyurethane or the like. Such material will be selected to be compatible with the purpose of implantation in a patient's body. The piston rod extends out of the upper cover in the same manner as has been described above with reference to the sleeve 10. The space 34 of the cylinder 36' is filled with a hydraulic liquid 37, which may circulate in a hydraulic circuit comprising the space 34 of the cylinder 36', the overflow ports 40 and 41 leading into storage spaces 38 and 39. The storage spaces are formed between indentations or grooves in the housing 32 and the envelope 33 and lead back to a low pressure pump chamber 45 through the ports 42 and 43 of a pump 44, preferably a microgear wheel pump. The low pressure pump chamber 45 is connected to a return flow channel 46 and to a control valve for the resetting of the piston 36. The control valve is not shown. The pump 44 is connected to the pressure chamber 47 below the piston 36 by means of an inflow channel 48 comprising a non-return valve not shown but well known.

The gear wheel pump 44 of the just described hydraulic system is driven by an electric motor 50 located in a cavity 49 in the housing 32. Preferably, the motor 50 drives the pump 44 through a reduction gear 51. The motor is energized from a battery 52 by means of an electronic control circuit 53, which may be activated externally as described above, for example, with magnetic field means for switching the motor on and off and for reversing its direction of rotation.

The sectional view of FIG. 4 shows the storage spaces 38 and 39 which due to the elasticity of the envelope 33 are also elastically yielding to some extent.

A further embodiment of a bone extension apparatus 10 is illustrated in FIGS. 5 and 6. In this embodiment, the extension member in the form of a piston rod 61 is driven by means of a bellows 62 connected by a three-way valve 63 to a pressure gas container 64. A locking disk 65 which may be either spring biased or threaded into an inner housing 65' assures a gas-tight seating of the pressurized gas container 64 against the three way valve 63. The outer housing 66 contains two coaxial cavities 67 and 68 interconnected by ports 69 for pressure equalization. A port 72 in the inner housing 65' provides communication between the cavities 67 and 68 and with the inner space of the bellows 62 depending on the position of the three-way valve 63. The pressure in the cavities 67 and 68 increases with an increasing extension of the bellows 62, whereby a respective pressure relief is accomplished for the bellows 62 upon a corresponding actuation of the three-way valve to thereby achieve a reverse movement of the piston rod 61 to a sufficient extent. Thus, the adjustment movement of the piston rod 61 is accomplished by the three-way valve 63 which may be magnetic valve and which is controlled by means of an electronic control device 70. The details of such a control device are well known. For example, an external magnetic field may be utilized to close contacts for energizing solenoids in the control device 70 which in turn will operate the three-way valve 63 in a well known manner. Two batteries 71 may be provided for supplying the energy required for the energization of the solenoids in the control device 70. These batteries 71 are arranged for easy replacement in the same manner as the pressure gas container 64 in the inner housing 65', which in turn is securely held in the housing 66 by a cover as described above with reference to FIG. 1.

The cavities 67 and 68 in the housing 66 provide space for arresting means, not shown, for locking the piston rod 61 in its extended positions as these positions are reached gradually or step by step. In its simplest form the arresting or locking mechanism may comprise a number of notches along the piston rod 61 preferably adjacent to the bellows 62 and magnetically operated stop means, which engage a notch and which may be operated through the control device 70 by electro-magnetic means such as a solenoid which would pull the stop means away from the piston rod 61 or permit the engagement of the stop and a notch in the piston rod 61. The batteries 71 would provide the necessary power to the control device 70 also for the operation of such stop mechanism.

All details not described with reference to FIGS. 5 and 6 are the same as those described with reference to FIGS. 1 to 4. The embodiment of FIGS. 5 and 6 is especially adaptable to an oval slender housing as best seen in FIG. 6.

FIGS. 7 and 8 illustrate yet another embodiment of an extension apparatus 80 according to the invention. This embodiment is especially compact. Similar to the embodiment of FIGS. 1 and 2, the embodiment of FIGS. 7 and 8 also comprises an extension member driven by a threaded spindle 81 cooperating with a sleeve 83 provided with a threaded bushing 82. The compact construction is especially ascertainable from the sectional view of FIG. 8. All elements which are the same as those in FIGS. 1 and 2 are not provided with reference numerals in FIGS. 7 and 8. A longitudinal hollow cavity 84 in the housing 85 provides space for a tongue 86 acting as a lever having a long end 86a and a short end 86b journaled to a journal pin 86c held in a boss 87. The tongue 86 may be made of magnetic material or it may have magnets attached thereto. The tongue 86 performs back and forth movements, for example, in response to corresponding movements of an external magnetic field symbolized by a block 86d. Means to generate such magnetic fields, for example, pulsed magnetic fields are well known in the art. The movement of the tongue 86 is limited by a spring 88 and a buffer 89.

The movement of the short end 86b of the tongue 86 is moved to rotate the spindle. For this purpose, a transmission linkage or joint 90 engages and entrains a reversible ratchet or clutch mechanism 91, which rotates the spindle 81 in accordance with the position of a selector switch 92. The selector switch 92 may be switched into a forward or reverse position for rotating the spindle clockwise or counter-clockwise. Mechanisms of this type are as such well known in the art. The selector switch 92 may, for example, be operated by an external magnetic field which is effective through the patient's tissue and through the housing 85 of the apparatus 80. The actuation of the switch 92 may also be accomplished by a frequency responsive device such as a mechanical vibrator which responds to the frequency of the tongue 86. Thus, if the tongue is actuated with one frequency, the spindle may rotate, for example, clockwise and it may rotate counter-clockwise if the tongue 86 is actuated by another frequency.

The embodiment of FIGS. 7 and 8 has an especially small volume due to its compactness. As a result, it is easily implanted. Yet another important advantage is seen in that the means for controlling the apparatus, as well as for energizing the apparatus drive are externally located so that a single magnetic field generator could be employed successively for actuating and controlling several extension devices implanted in different patients. Moreover, the external arrangement of the power drive and control means does not call for a compact construction of these external means, whereby these external means may be produced at relatively low costs.

Incidentally, the pressurized gas will, for example, be $CO_2$, which is body-compatible and hence suitable for implantation for driving the bellows or even a pneumatically operated piston cylinder arrangement.

The control device which may be employed with any of the present embodiments for controlling either the electric motor drive or the hydraulic or pneumatic drive will preferably comprise timer means for adjusting the extension stroke with respect to time as well as with respect to its length. To this end the control means will include electrically or fluidically controlled valves and or switches, as well as a clock pulse generator.

Another advantage of the invention is seen in that a resetting of the extension stroke may easily be accomplished for the purpose of corrections, for example, to prevent trophic impairments. It is also advantageous that the connecting elements 14 and 15 are implantable along with the entire apparatus, so that any levering actions are minimized and thus the patient is enabled to perform more vigorous exercises, especially since with this arrangement it is now possible to provide a force locking and/or a form locking connection between the proximal and distal bone portions and the respective connecting elements of the present apparatus.

Incidentally, FIG. 5a shows the operation of the double three way valve 63 in more detail. Electronic timers 101 and 102 energize at different times the solenoids 103 and 104 to operate the valve 63. In the shown rest position of valve 63 its ports 109, 110, and 164 are closed. Energizing the solenoid 103 moves the valve actuator 111 to the left thereby providing communication between ports 109 and 164 as shown at the right hand end of the valve 63. Thus, gas flows from container 64 into bellows 62 raising piston rod 61. When thereafter the solenoid 104 is energized, actuator 111 is moved to the right connecting ports 109 and 110 as shown at the left hand end of the valve 63. Thus, the pressure between bellows 62 and space 68 is equalized through ports 69 whereby piston rod 61 may be pushed back to its starting position.

Although the invention has been described with reference to specific example embodiments, it will be understood, that it is intended to cover all modifications and equivalents within the scope of the appended claims.

What is claimed is:

1. An apparatus, especially for osteotomic surgery, comprising a housing, extension means movably supported in said housing and including an extension member movably extending out of said housing, power drive means also supported in said housing and operatively connected to said extension means for moving said extension member, means sealing said housing to form an implantable structural unit, said power drive means comprising a drive motor and a source of power operatively connectable to said motor, said apparatus further comprising implantable control means also supported in said housing and responsive to external actuation, said control means being operatively connected to said power drive means inside said implantable structural unit, and implantable connecting means secured to said housing for connection of the apparatus to a bone.

2. The apparatus according to claim 1, wherein said source of power comprises magnetic field means located externally of said housing said power drive means comprising motor means inside said housing and responsive to said externally located magnetic field means for moving said extension member.

3. The apparatus according to claim 1, wherein said power drive means comprise electric motor means, said source of power including electric power means located in said housing and operatively connected to said electric motor means, and reduction gear means also located in said housing and operatively connecting said electric motor means to said extension means for moving said extension member.

4. The apparatus according to claim 1, wherein said power drive means comprise pressure operated motor means located in said housing, said source of power including a source of pressure also located in said housing, and means operatively connecting said source of pressure to said pressure operated motor means.

5. The apparatus according to claim 4, wherein said source of pressure comprises an implantable pressurized gas container filled with a body compatible gas such as $CO_2$.

6. The apparatus according to claim 1, wherein said source of power includes a source of pressure and a hydraulic circuit with a pressurized hydraulic liquid in said hydraulic circuit.

7. The apparatus according to claim 6, wherein said source of pressure includes a hydraulic pump located in said housing and operatively connected to said hydraulic liquid circuit, said pump forming an integral part of the implantable structural unit.

8. The apparatus according to claim 7, further comprising control means operatively connected to said power drive means, said control means comprising valve means arranged in said connecting means between said pressure operated motor means and said source of pressure, and timer means operatively connected to said valve means for determining the timing of a valve operation and its duration whereby the extent of movement of said extension member may be controlled.

9. The apparatus according to claim 1, wherein said power drive means comprise magnetically operable lever means, ratchet means connected to said lever means, clutch means interconnecting said ratchet means and said extension means, and magnetically operable switch means operatively connected to said clutch means for rotating said extension means clockwise or counterclockwise.

10. The apparatus according to claim 1, wherein said power drive means are reversible for moving said extension member in a reverse direction.

11. The apparatus according to claim 1, further comprising a body compatible coating enveloping said housing.

12. The apparatus according to claim 1, wherein said extension means comprise a threaded spindle rotatably supported in said housing, said extension member comprising a threaded sleeve engaging said spindle and extending out of said housing, said power drive means being arranged to rotate said spindle.

13. The apparatus according to claim 12, wherein said power drive means comprise an electric motor having a shaft, a battery connectable to said motor, and gear means connecting said motor shaft to said spindle.

14. The apparatus according to claim 13, wherein said power drive means comprise magnetically operable ratchet means connected to said spindle.

15. The apparatus according to claim 1, wherein said extension means comprise a bellows, said power drive means comprising a source of gas under pressure, valve means connecting said pressure source to said bellows, and means operatively connecting said bellows to said extension member.

16. The apparatus according to claim 1, wherein said extension means comprise piston and cylinder means, said extension member comprising a piston rod connected to said piston and extending out of said housing, said power drive means comprising a pump, hydraulic circuit means connecting said pump to said cylinder, an electric motor having a shaft, gear means connecting said motor shaft to said pump, and battery means connectable to said electric motor.

* * * * *